US006106772A

United States Patent [19]

Kohler et al.

[11] Patent Number: 6,106,772

[45] Date of Patent: Aug. 22, 2000

[54] INJECTOR IMPINGER

[75] Inventors: James P. Kohler, Laguna Hills; Harold R. Williams, San Clemente, both of Calif.

[73] Assignee: Ethicon, Inc., Sommerville, N.J.

[21] Appl. No.: 09/103,126

[22] Filed: Jun. 23, 1998

Related U.S. Application Data

[60] Provisional application No. 60/050,983, Jun. 23, 1997.

[51] Int. Cl.[7] .............................. A61L 2/20; B01D 45/08

[52] U.S. Cl. ............................ 422/28; 422/292; 422/305; 55/434.2; 55/462; 55/463; 239/462; 239/524

[58] Field of Search .................................... 239/461, 462, 239/504, 518, 524; 55/434, 437, 434.2, 463, 462; 422/28, 292, 305

[56] References Cited

U.S. PATENT DOCUMENTS 2,954,842 10/1960 Coulter .
3,570,221 3/1971 Oliver .
4,014,671 3/1977 Andro et al. .......................... 55/463 X
4,643,876 2/1987 Jacobs et al. ............................ 422/22
4,913,196 4/1990 Williams et al. .
4,938,262 7/1990 Williams et al. ..................... 422/32 X
5,078,976 1/1992 Shibauchi et al. ...................... 422/298

*Primary Examiner*—Elizabeth McKane
*Attorney, Agent, or Firm*—Knobbe, Martens, Olson and Bear, LLP

[57] ABSTRACT

A sterilizing system for receiving a stream of solid-stabilizer-containing fluid and sterilizing an article comprises a chamber for receiving the article and an injection assembly coupled to the chamber for generating and introducing a fluid jet into the chamber. The system particularly comprises an injector impinger for removing particulates and liquid droplets from the solid-stabilizer-containing fluid by causing a sudden change of the stream line direction of the fluid jet. The injector impinger is positioned between the injection assembly and the article, so that the fluid jet can not reach the article without first interacting with the injector impinger. A method for removing particulates from a solid-stabilizer-containing fluid in a sterilizing process comprises the steps of providing the fluid, vaporizing the fluid, forming a vapor stream from the vaporized fluid, and removing the particulates and the droplets from the vapor stream by causing a sudden change of direction of stream line of the vapor stream.

19 Claims, 4 Drawing Sheets

INJECTOR IMPINGER

RELATED APPLICATIONS

This application claims the benefit of the Provisional Application No. 60/050983, entitled INJECTOR IMPINGER, filed Jun. 23, 1997.

BACKGROUND OF THE INVENTION

The present invention relates to a system for injecting or dispensing controlled volumes of fluid, particularly for automated injections of very small amounts of fluid into a chamber for sterilizing items such as medical instruments. The present invention particularly relates to a system for removing particulates from the injected fluid and preventing the particulates from depositing on surfaces of the items to be sterilized.

Various sterilants or sterilizing fluids have been used to sterilize medical instruments. One effective way of sterilization is to sterilize the item with a sterilant vapor. In this sterilization process, the item to sterilized is placed in a vacuum chamber. A liquid sterilant is introduced into the vacuum chamber and vaporized therein, so that the item is sterilized by the sterilant vapor.

U.S. Pat. No. 4,643,876 discloses a sterilization method and apparatus. In this method, a sterilizing agent such as hydrogen peroxide is introduced into an evacuated sterilizing chamber where it is vaporized and allowed to disperse onto the items to be sterilized. After a desired period of time, electrical energy is then applied in the chamber to ionize the gas to form a plasma at a power level sufficient to achieve sterilization.

U.S. Pat. No. 4,938,262 and U.S. Pat. No. 4,913,196 issued to the same inventors disclose a pumping apparatus for the fluid injection in a sterilization system, and a method of pumping a sterilizing liquid into an evacuated sterilizing chamber containing an article to be sterilized.

The pumping apparatus for the fluid injection system disclosed in U.S. Pat. No. 4,938,262 provides a fluid supply in the form of a prepackaged closed cell containing a known volume of fluid. The apparatus further includes a mechanism for receiving and positioning the cell, and a cell opener assembly cooperating with the mechanism for penetrating the cell to form an outlet from the cell. A device cooperating with the cell and the receiving mechanism forces the entire volume of fluid out of the cell, thus providing a convenient pumping apparatus for providing a known quantity of fluid.

The systems provided in the above U.S. patents are effective, and have number of advantages over other known systems. Consequently, those sterilization systems disclosed in the above mentioned U.S. patents have been commercialized.

However, further improvements are needed to overcome the disadvantages of the existing vapor sterilization systems. One common problem of existing vapor sterilization system is the deposition of particulates on the surface of the item to be sterilized because stabilizers present in the liquid sterilant, which gives the sterilized item unpleasant and unclean appearance.

Thus, there is a need for a method and apparatus, which eliminates the deposited particulates on the surface, and meanwhile maintains sterilization efficiency.

SUMMARY OF THE INVENTION

The present invention presents a significant improvement to existing sterilization systems, especially those described in U.S. Pat. No. 4,643,876, 4,938,262, and 4,913,196 by eliminating or significantly reducing particulate deposition on surfaces of items to be sterilized. These two U.S. patents are incorporated herewith by reference in their entirety.

The present invention provides a simple and economical way to remove particulates from a fluid stream before it reaches the article to be sterilized and significantly reduce the solid residue deposition on surface of the article to be sterilized. According to the present invention, an injector with a special impinger is provided. The impinger is placed across the pathway of sterilizing fluid stream injected from an inlet of the injector. Before reaching to the impinger a significant portion of the liquid sterilant should be vaporized so that a vapor stream of the sterilant is generated. The impinger provides a surface of suitable shape facing the vapor stream at an appropriate angle. When the stream of the sterilant vapor approaches the impinger surface, the stream line will change direction sharply near the impinger surface. During the vaporizing process, stabilizers or other solid additives initially dissolved in the liquid sterilant will be separated from the fluid phase as tiny particulates and travel with the vapor stream. Because their mass, those particulates will not be able to follow the stream line when the stream line takes a sharp turn near the impinger surface. Instead, those particulates will keep moving toward the impinger surface and are collected on the impinger surface. The collecting efficiency can be affected by many factors, such as dimension, shape, roughness, or material of the impinger surface, the angle between the impinger surface and the stream line, the velocity of the stream, the vapor/liquid ratio of the stream.

One aspect of the present invention relates to a sterilizing system for receiving a stream of solid-stabilizer-containing fluid and sterilizing an article. The sterilizing system comprises:

- a chamber, which may further comprise an electrode for generating plasma;
- an injection assembly connected to the chamber sealed and normally closed so that a vacuum may be maintained in the chamber;
- an injector impinger having an surface, mounted inside the chamber and positioned between the injection assembly and the article.

The injection assembly has a body, a fluid inlet passage, a vaporizer bowl, a vapor passage for introducing vapor from the vaporizer bowl to the chamber and forming a vapor jet, and a male thread at the bottom portion of the injection assembly. The injection assembly further comprises a heating device secured to its body.

The injector impinger has a conically-shaped central section, a disk section surrounding said conically-shaped section, and a hole with a female thread in the center of the injector impinger, and is secured to said injection assembly through said male and female threads so that the upper surface of the disk section of the injector impinger is substantially perpendicular to the stream line of the vapor jet and prevents the vapor jet from directly impinging the article. The injector impinger is made of plasma compatible materials, such as polypropylene.

The fluid agent can be any compound suitable for sterilization. Preferably, the fluid agent is liquid hydrogen peroxide, more preferably, is substantially pure hydrogen peroxide. Any solid stabilizer suitable for hydrogen peroxide can be used. A very effective solid stabilizer used in this invention is purchased from FMC.

Another aspect of the present invention provides a method for removing particulates from a solid-stabilizer-containing fluid in a sterilizing process. The method comprises the steps of:

introducing a liquid phase fluid containing dissolved solid stabilizer;

vaporizing said liquid phase fluid forming a vapor stream containing particulates mainly formed from the solid stabilizer;

removing the particulates from the vapor stream and entrained liquid droplets by sudden change of direction of stream line of said vapor stream.

The vaporizing step is conducted in a chamber under vacuum of about 0–1 torr, preferably 0–400 mtorr, before the liquid is injected into the chamber, and at a temperature in the range of about 20–70 C.

The step of removing particulates is conducted by putting an injector impinger between the vapor stream and a downstream article to be sterilized, so that the vapor stream can not reach the article without impinging the injector impinger first. Preferably, the injector impinger is positioned so that the stream line of the vapor stream is substantially perpendicular to the injector impinger's surface facing upstream in terms of the travel direction of the vapor stream.

Another aspect of the present invention provides an injector impinger for removing particulates from a fluid stream introduced into a sterilization system, said sterilization system comprising a fluid injection assembly, a sterilizing chamber for holding vacuum, an electrode installed in the chamber for generating plasma, and an article to be sterilized within the chamber. The injector impinger comprises:

a base plate positioned between the injection assembly and the article;

a connecting device for securing the injector impinger in position.

The base plate has a conically-shaped central section and a flat disk section surrounding the central section, and the connecting device is a threaded through hole positioned in the center of the base plate. The injector impinger is made of plasma compatible materials, preferably, plastic material such as polypropylene.

Still another aspect of the present invention provides a liquid injection combination for vaporizing injected liquid and removing particulates from generated vapor from the injected liquid. The combination comprises:

a liquid inlet for receiving the injected liquid;

a vaporizer bowl for vaporizing the injected liquid;

a vapor passage providing a passage for vapor generated from the injected liquid and forming a vapor stream;

a injector impinger having a surface positioned against stream line of the vapor stream, so that particulates traveling with the vapor stream and entrained liquid droplets are separated from the vapor stream and retained on the surface of the injector impinger.

DETAILED DESCRIPTION OF THE PREFERRED EMBODIMENT

The existing sterilizing systems using liquid hydrogen peroxide as sterilant, such as those described in the U.S. patents cited above, are very effective. However, a stabilizer is usually added to the hydrogen peroxide during its storage to stabilize the hydrogen peroxide, and most such stabilizers are in solid state. When used, the solid stabilizers is dissolved in hydrogen peroxide, and the liquid hydrogen peroxide with dissolved stabilizer is injected into a sterilizing chamber where the liquid hydrogen peroxide or its solution is vaporized under vacuum and/or elevated temperature. During this vaporizing process, the dissolved solid stabilizer separates from the liquid phase and forms tiny particulates traveling with the vapor stream and with any incompletely vaporized liquid droplets generated from the injected liquid hydrogen peroxide, and deposits on the surfaces of articles to be sterilized in the sterilizing chamber. The deposition of the solid stabilizer residue on the article surface is very undesirable, because it presents an unsightly product image to hospital personnel.

Figure 1:
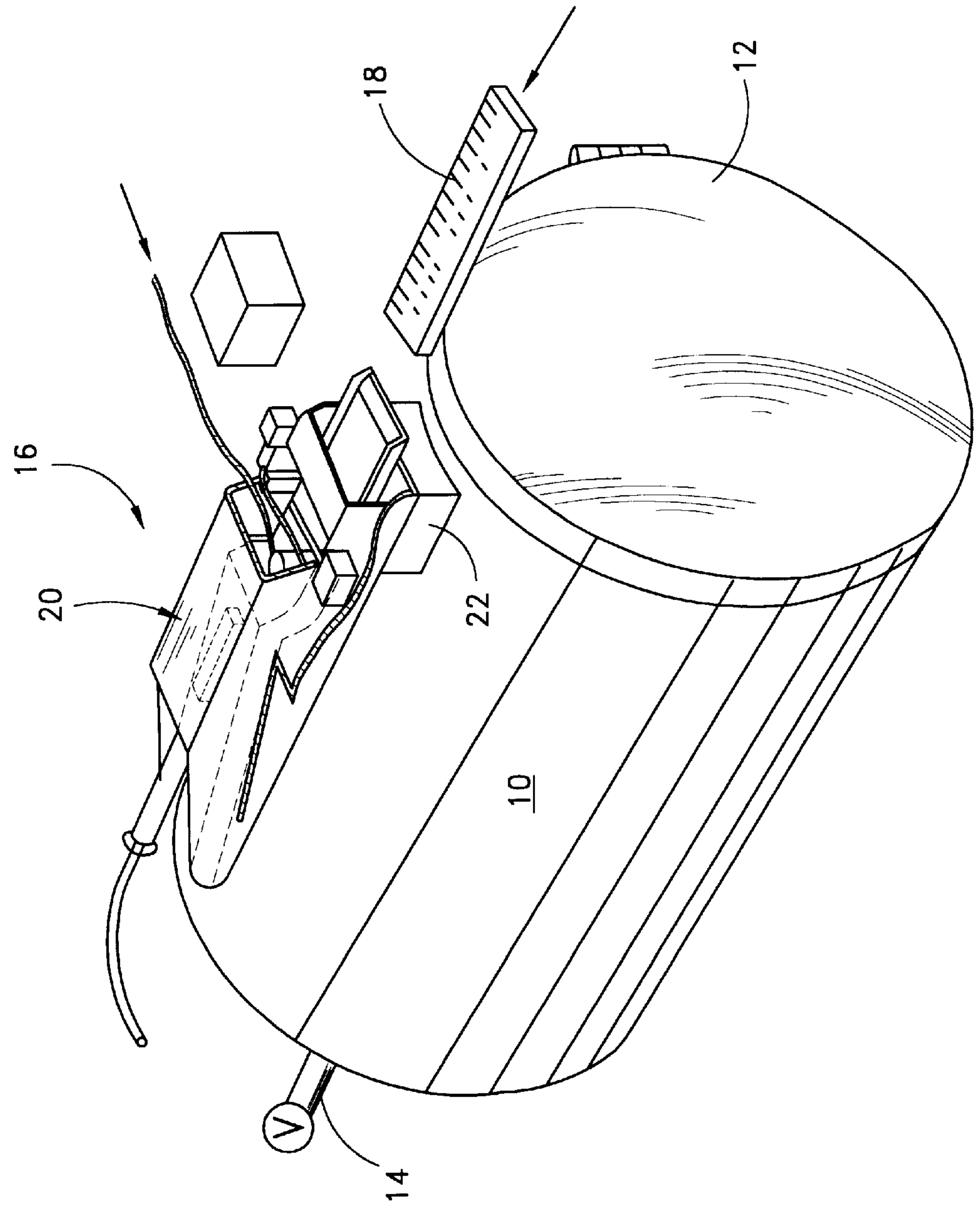
FIG. 1 is a schematic view of the sterilizing system illustrating the system of the present invention.

Referring to FIG. 1, there is schematically illustrated a cylindrical chamber 10 having a door 12 on one end. The chamber is connected to a suitable vacuum source by way of a conduit 14. The chamber is adapted to receive items to be sterilized, such as surgical instruments, in accordance with a method outlined in U.S. Pat. No. 4,643,876 which is incorporated herewith by reference, wherein a liquid such as hydrogen peroxide is introduced into the chamber. For delivering such fluid, in accordance with the present invention, there is provided a fluid injection system 16 positioned adjacent to the chamber 10.

The system includes a cassette or cartridge 18 containing the fluid to be injected, a cassette receiving, positioning and clamping mechanism 20, and a fluid injector valve assembly 22 mounted on and interconnected with the chamber. An injector impinger 200 (not shown) is secured to the fluid injector valve assembly 22 or to other part of the chamber. The fluid injector system 16 can be thought of as a pump in which the cassette 18 is inserted into the cassette receiving mechanism 20 and doses of the media contained in the cassette are automatically injected into the chamber during automated sterilizing cycles.

The system described above is similar to the system disclosed in U.S. 4,938,262 which is incorporated herewith by reference, except for the addition of an injector impinger. The significant advantage of the system of the present invention results from the addition of the injector impinger 200 inside the chamber. For example, the injector impinger can be positioned at the vapor outlet of the fluid injector valve assembly 22 with or without modifications to the structure of the fluid injector valve assembly 22.

Figure 2:
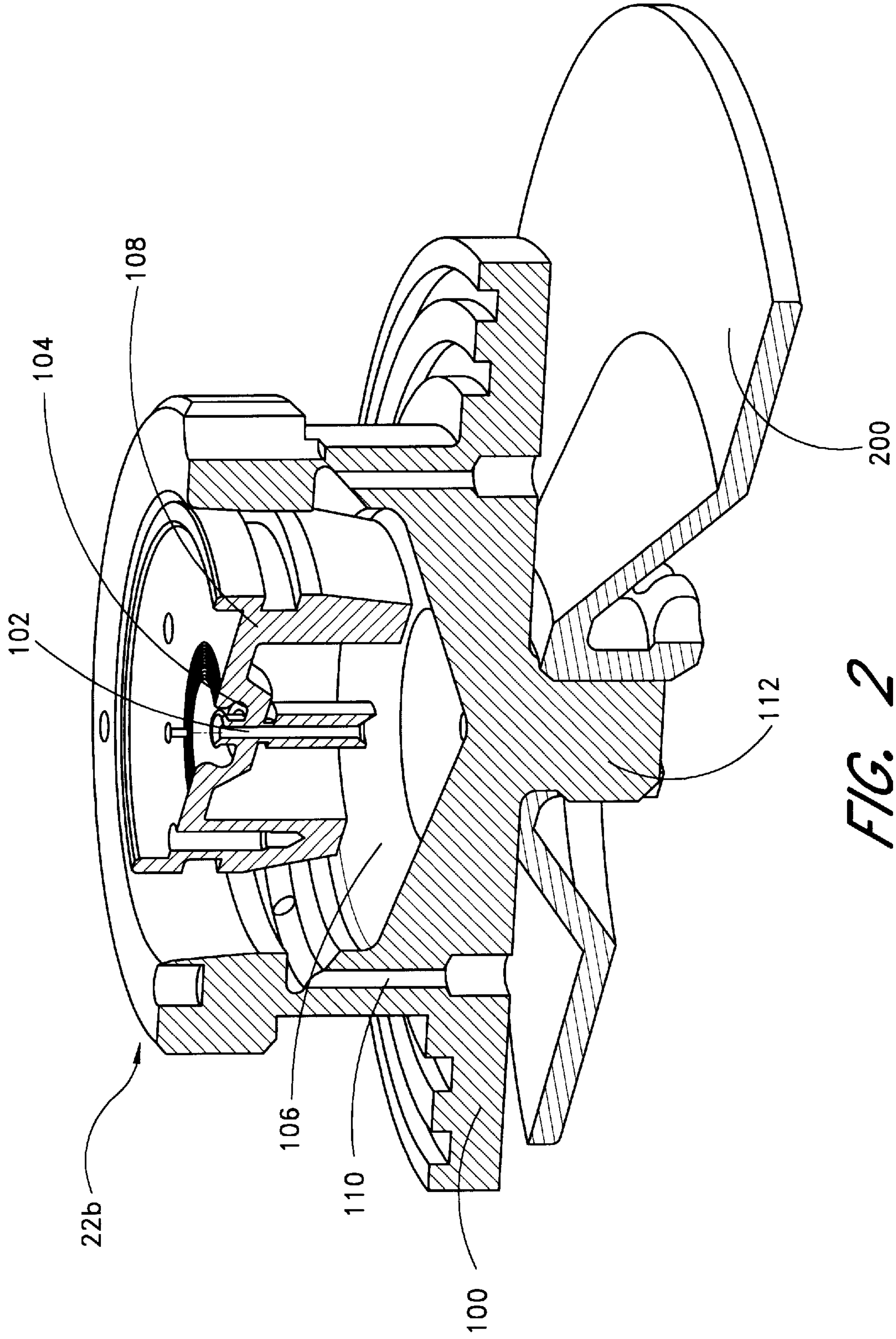
FIG. 2 is a cross-sectional view of the injection assembly connected to the injector impinger in the sterilizing system of the present invention.

Other modifications on the system of U.S. Pat. No. 4,938,262, in addition to the introduction of an injector impinger, are made in the present invention. Thus, in one preferred embodiment of the present invention, the fluid injector valve assembly 22 is replaced by an injection assembly **22*b* as shown in FIG. 2**. The sterilizing chamber of the present invention may also further include an electrode for generating plasma, and has a rectangular cross-sectional area or any other appropriate shape.

In one preferred embodiment, the injection assembly **22*b* is mounted and sealed to the chamber 10. The injection assembly 22*b* can be further provided with a pressure relief valve connecting to a liquid injection device. As shown in FIG. 2, the injection assembly 22*b* has an body 100 which is mounted and sealed to the chamber 10. A valve outlet passage 102 for receiving liquid hydrogen peroxide or other fluid from a liquid injection device such as that shown in FIG. 1. An 0-ring seal 104 is provided to secure the sealing around the valve outlet passage 102. The valve outlet passage intrudes into a vaporizer bowl 106 where the injected liquid is vaporized. The vaporizer bowl is defined by the body 100 and a second piece 108. The valve outlet passage 102 is also located at the center of the second piece 108. Vapor passage 110 is provided to connect the vaporizer bowl 106 to the chamber 10. Vapor generated from the injected liquid in the vaporizer bowl 106 travels through the vapor passage 110 from the vaporizer bowl 106 to the chamber 10 and forms a vapor stream or vapor jet together with solid stabilizer residue particulates and entrained liquid droplets. At the bottom portion of the body 100, there is an extrusion part with a male thread 112 for receiving the injector impinger. The injection assembly is also equipped with a heating device (not shown) for keeping a desired temperature at the vaporizer bowl 106 and the valve outlet passage 102**. The operation temperature may vary, preferably in a range of about 20–80, more preferably about 55–65° C.

Figure 3:
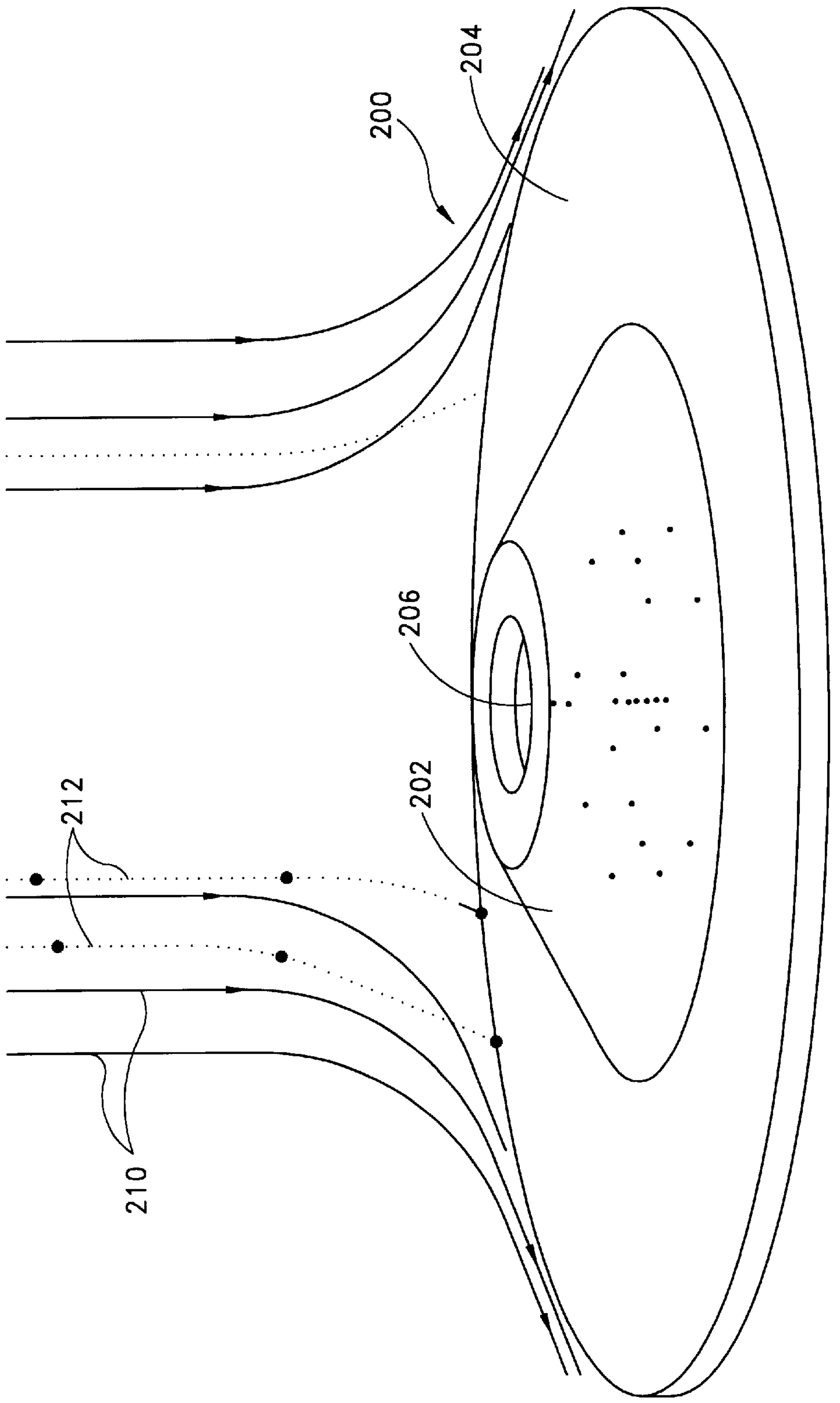
FIG. 3 is a schematic view of the injector impinger of the present invention.
Figure 4:
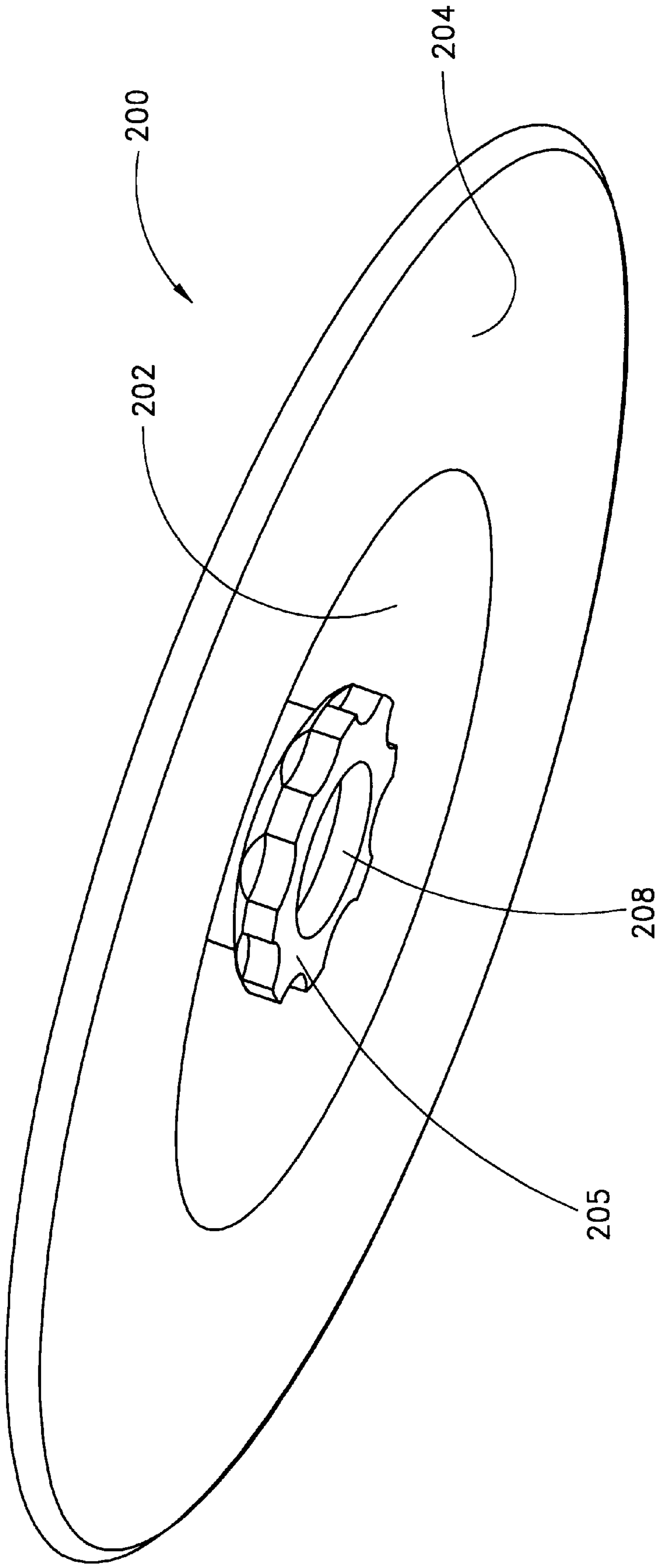
FIG. 4 is a isometric view of the injector impinger of the present invention.

An injector impinger 200 is attached to the injection assembly as shown in FIG. 2. Referring to FIGS. 3 and 4, the injector impinger has a conically-shaped central section 202, a flat disk section 204 surrounding the conically-shaped section 202, and a downward extrusion piece 205 in the center with an elongated hole 206 and a female thread 208 on the inner wall of the elongated hole 206. The injector impinger 200 is secured to the body 100 through the male thread 112 of the body 100 and the female thread 208 of the injector impinger 200. If desirable, the injector impinger can be provided with a temperature control mechanism to control its temperature. For example, the injector impinger can be made hollow, and cooling or warming fluids are filled into or circulated through the hollow body of the injector impinger.

The vapor stream together with the solid stabilizer residue particulates and entrained liquid droplets enters the chamber 10 through the vapor passage 110, forming a vapor stream or vapor jet. The vapor jet travels at a velocity determined by several factors including the dimension of the vapor passage 110, the pressure drop between the vaporizer bowl 106 and the chamber 10, and the temperature of the vapor jet. The vapor jet velocity will change as the vapor jet travels away from the outlet of the vapor passage.

Although the present invention is not limited to any theory, it is believed that the particulate removing mechanism of the present invention is based on fluid dynamic principles. Thus, when the vapor jet is entering the chamber 10 from the outlet of the vapor passage, the vapor entrained liquid droplets and the tiny particulates travel along straight stream lines at certain velocity. Once the vapor jet is disturbed by an object, the stream line 210 of the vapor jet will change direction as shown in FIG. 3 according to the shape of the surface of the object. Because of their mass, the particulates and entrained liquid droplets can no longer follow the stream line 210. Instead, the particulates and entrained liquid droplets will travel along a path 212 between the straight stream line and the changed curved stream line 210, and impinge the surface of the injector impinger 200. The particulates will stick to the surface of the injector impinger. Apparently, velocity of the vapor jet is an important factor affecting particulate removing efficiency. Thus, the distance between the particulate-collecting surface of the injector impinger and the outlet of the vapor passage will affect particulate-removing efficiency. The shape of the particulate-collecting surface and the angle between the stream line and the surface also have important effects. Preferably, the particulate-collecting surface is positioned perpendicular to the stream line.

Other options are obvious based on the teaching of the present invention. For example, the injector impinger does not have to be a single piece, does not have to be mounted to the injection assembly 22*b*, and does not have to be the shape as described earlier. The vapor passage 110 does not have to be vertical. In stead, it can be directed to the side wall of the chamber 10, and the particulates are collected in an injector impinger accordingly positioned. The injector impinger can be made of any metal, ceramic, and plastic materials. However, if the injector impinger is used with plasma, it should be made of plasma-compatible materials such as plastics. In a preferred embodiment of the present invention, the injector impinger is made of polypropylene.

In the use of the system of the present invention, vacuum is applied to the chamber 10 by way of the conduit 14. And the pressure in the chamber 10 and the vaporizer bowl 106 is preferably kept below about 1 torr, more preferably between about 0–400 mtorr before the liquid agent is injected. Then, a liquid agent such as hydrogen peroxide with dissolved solid stabilizer such as FMC is injected into the vaporizer bowl through valve outlet passage 102. The liquid injection assembly described in U.S. Pat. No. 4,913,196 can be used to make the injection. In order to facilitate the evaporation of the liquid agent, vaporizer bowl 106 of the injection assembly 22*b* can be heated to a desired temperature, preferably 20–80° C., more preferably 50–70° C. In one preferred embodiment, the vaporizer bowl is heated to 60° C. The generated vapor stream flows from the vaporized bowl to the chamber 10 through vapor passage 110 under a pressure drop between the vaporizer bowl 106 and the chamber 10. The pressure drop is caused by the rapid evaporation of the liquid agent. The vapor stream with solid stabilizer particulates and entrained liquid droplets impinges the upper surface of the injector impinger 200. A significant percentage of the particulates will be separated from the vapor stream and collected on the surface. As the vapor stream continue to travel along a stream line affected or confined by the injector impinger, a portion of the particulates also continue to follow the vapor stream. In the preferred embodiment shown in FIG. 2, the stream line of the vapor stream will follow the wall of the chamber 10 after impinging the injector impinger 200. Thus, the remaining solid stabilizer particulates will deposit on the walls and bottom of the chamber. After certain cycles of sterilizing operation, the injector impinger can be easily replaced and cleaned. The walls and the bottom of the chamber 10 are also easy to clean. Therefore, the particulate deposition on surfaces of the items to be sterilized is eliminated or at least significantly reduced.

While the invention for removing particulates from a fluid has been described in connection with injecting liquid into a chamber for a sterilizing cycle, it should be understood that the system is also useful for removing particulates from a liquid to be injected in a process other than sterilization. Also, the system can be used to remove particulates from a gas or mist injected into containers other than vacuumized chambers. Various modifications can be made without departing from the spirit and scope of the present invention.

What is claimed is:

1. A sterilizing system for receiving a stream of fluid containing solid particulates and sterilizing an article comprising:

a chamber for receiving the article;

an injection assembly coupled to the chamber for generating and introducing a fluid jet into said chamber; and an injector impinger positioned between said injection assembly and the article, so that the fluid jet can not reach the article without first interacting with the injector impinger, wherein said injector impinger is located outside said injection assembly and wherein said injection assembly comprises:

a fluid inlet passage for introducing the fluid;

a vaporizer bowl for vaporizing at least a portion of the fluid; and a vapor passage for introducing the at least partially vaporized fluid from the vaporizer bowl to the chamber and forming the fluid jet.

2. A sterilizing system of claim 1, wherein said vaporizer bowl is operated under a first pressure lower than atmospheric pressure, said chamber is operated under a second pressure lower than said first pressure.

3. A sterilizing system of claim 1, wherein the injector impinger has a impinging surface for interacting with the fluid jet and collecting particulates contained in the fluid jet, said surface faces the fluid jet and forms an angle with stream line of the fluid jet, such that direction change of said stream line caused by said surface is sharp enough to cause particulates unable to follow the changed stream line and stick on said surface.

4. A sterilizing system of claim 3, wherein the injector impinger has a truncated cone-shaped central section with a hole for connecting said injection assembly, and a disk section surrounding said cone-shaped central section, said disk section provides said impinging surface substantially perpendicular to said stream line.

5. A sterilizing system of claim 3, wherein the injector impinger is made of plasma compatible materials.

6. A sterilizing system of claim 5, wherein the injector impinger is made of polypropylene.

7. A sterilizing system of claim 3, wherein the chamber further comprises an electrode for generating a plasma.

8. A sterilizing system of claim 3, wherein the injection assembly further comprises a heating device secured to its body.

9. A sterilizing system of claim 3, wherein the fluid jet comprises hydrogen peroxide and solid particulates, wherein the solid particulates comprise hydrogen peroxide stabilizer.

10. A method for removing solid particulates from fluid containing solid particulates in a sterilizing process, comprising the steps of:

providing said fluid;

vaporizing said fluid from an injection assembly;

forming a vapor stream from said vaporized fluid, said vapor stream containing solid particulates mainly formed from a solid stabilizer and entrained liquid droplets; and removing the solid particulates from the vapor stream by causing a sudden change of direction of stream line of said vapor stream with an impinger located outside said injection assembly.

11. A method of claim 10, wherein the vaporizing step is conducted under a vacuum in the range of about 0–1 torr.

12. A method of claim 10, wherein the vaporizing step is conducted at a temperature in the range of about 20–70° C.

13. A method of claim 10, wherein the step of removing the particulates and the droplets is conducted by placing an impinging surface between the vapor stream and an article to be sterilized, so that the vapor stream can not reach the article without impinging the impinging surface first.

14. A method of claim 13, wherein the impinging surface is substantially perpendicular to stream line of the vapor stream.

15. A method of claim 10, wherein the solid stabilizer is a hydrogen peroxide stabilizer.

16. A method of claim 10, wherein the fluid comprises hydrogen peroxide.

17. An injector impinger for removing solid particulates from a fluid stream introduced into a sterilization chamber for sterilizing an article, said fluid stream being introduced from an injector assembly, said injector impinger comprising:

an impinging surface facing said fluid stream and positioned upstream of the article, so that said impinging surface causes a sudden change of direction of stream line of the fluid stream before said fluid stream reaches the article, wherein said impinging surface is located outside of the injector assembly; and a connecting device for securing the impinging surface in position, wherein the injector impinger is made of plasma compatible materials.

18. An injector impinger of claim 17, wherein the injector impinger has a truncated cone-shaped central section and a disk section surrounding said cone-shaped central section, said disk section provides said impinging surface substantially perpendicular to said stream line, and said connecting device comprises a central hole in the truncated cone-shaped central section.

19. A sterilizing system for receiving a stream of fluid containing solid particulates and sterilizing an article comprising:

a chamber for receiving the article;

an injection assembly coupled to the chamber for generating and introducing a fluid jet into said chamber;

an injector impinger positioned between said injection assembly and the article, so that the fluid jet can not reach the article without first interacting with the injector impinger, wherein said injector impinger is located outside said injection assembly; and a heating device secured to a body of the injection assembly.

* * * * *